United States Patent [19]

Wan et al.

[11] Patent Number: 5,487,986

[45] Date of Patent: Jan. 30, 1996

[54] METHOD FOR INCREASING PLASMID YIELD

[75] Inventors: Nick C. Wan, Newton; Jason C. Goodrick, Cambridge, both of Mass.

[73] Assignee: Genzyme Corporation, Cambridge, Mass.

[21] Appl. No.: 209,581

[22] Filed: Mar. 10, 1994

[51] Int. Cl.$^6$ .............................. C12P 19/34; C12N 1/20
[52] U.S. Cl. ...................................... 435/91.1; 435/252.33
[58] Field of Search .......................... 435/252.33, 252.3, 435/69.1, 91.1

[56] References Cited

U.S. PATENT DOCUMENTS

| | | | |
|---|---|---|---|
| 3,753,723 | 8/1973 | Henderson et al. | 99/9 |
| 4,656,131 | 4/1987 | Kitano et al. | 435/68.1 |
| 4,681,852 | 7/1987 | Tribe | 435/108 |
| 5,017,482 | 5/1991 | Katsumata et al. | 435/114 |
| 5,032,514 | 7/1991 | Anderson et al. | 435/138 |
| 5,219,746 | 6/1993 | Brinegar et al. | 435/172.3 |

OTHER PUBLICATIONS

Aaronson, *CRC Handbook of Microbiology*, vol. I, Laskin et al. eds., CRC Press, Cleveland, pp. 725–730.

Felgner, P. et al. (1987) "Lipofection: A highly efficient, lipid–mediated DNA–transfection procedure" *Proc. Nat. Acad. Sci., USA*, 84 (Nov.): 7413–7417.

Hofmann, K. H., et al. (1990) "Amplification of pBR322 Plasmid DNA in *Escherichia coli* relA Strains During Batch and Fed–Batch Fermentation" *J. Basic Microbiol.* 30(1):37–41.

Hyde, S. et al. (1993) "Correction of the ion transport defect in cystic fibrosis transgenic mice by gene therapy" *Nature*, 362 (Mar. 18): 250–255.

*Primary Examiner*—Mindy Fleisher
*Assistant Examiner*—James Ketter
*Attorney, Agent, or Firm*—F. Brad Salcedo

[57] ABSTRACT

This invention relates to an aqueous medium formulation which is capable of allowing the growth of a plasmid-producing host cell to a density greater than 30 at a reading of 600 nm and, in addition, enhancing plasmid production beyond that which would be expected at the cell densities achieved. The medium of the present invention comprises a carbon source in the concentration range of about 20 to about 40 grams per liter of the water component of the medium.

3 Claims, 1 Drawing Sheet

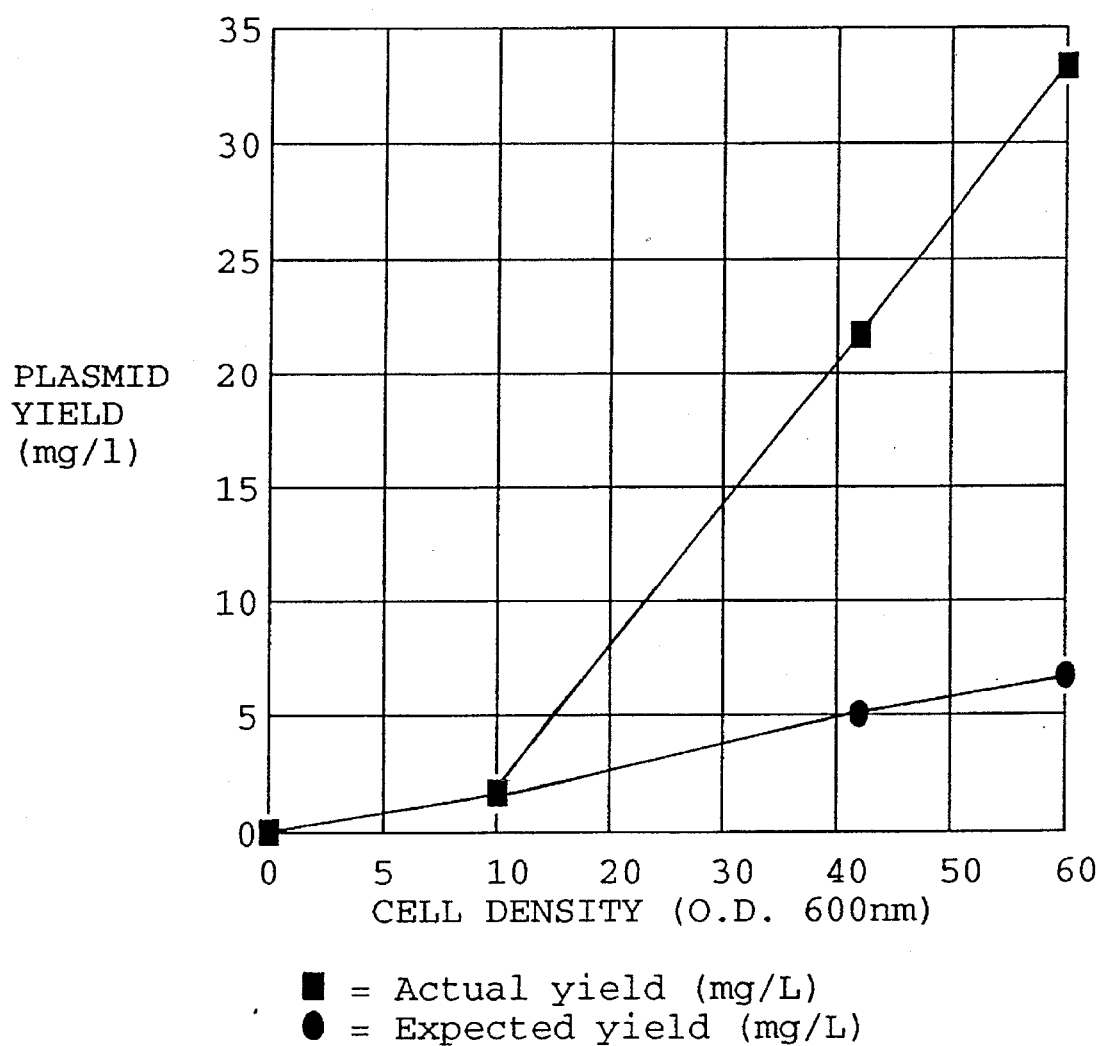
*The Figure*

METHOD FOR INCREASING PLASMID YIELD

BACKGROUND OF THE INVENTION

Increasing attention has been focused on the delivery of genes as therapeutic agents (i.e., gene therapy) for the treatment of gene-associated diseases. In particular, researchers have been studying the use of non-viral methods of delivery, due to safety concerns with using potentially infectious viruses. One of the most promising non-viral methods in gene therapy is the use of cationic lipids as a delivery vehicle (Felger, *Proc. Natl. Acad. Sci.*, 84:7413–7417, 1987). The cationic lipids bind with negatively charged DNA and facilitate entry of the DNA into target cells. Successful delivery of genes via lipids into airway epithelia of rodents (Hyde, *Nature*, 362:250–255, 1993) have been reported. The gene of interest is generally incorporated into plasmids which can be produced and isolated from bacterial cells. Cationic lipids are generally synthesized chemically or isolated from natural sources using various methods known in the art. If lipid delivery of genes proves to be effective, huge quantities of plasmids will be required for future gene therapy. However, current methods for producing genes may impede progress in this field.

Currently there are very few reports on plasmid yield enhancement. One method involves the addition of a protein inhibiting drug, chloramphenicol, into a host culture (Maniatis et al. *Molecular Cloning, A Laboratory Manual*, 2d, Cold Spring Harbor Laboratory Press, 1989). This approach does not increase plasmid yield significantly and, in addition, chloramphenicol is toxic to humans (AHFS Drug Information, *American Society of Hospital Pharmacists*, 1994). In another method, the plasmid producing cells are grown in a fed batch mode (Hofman et al., *J. Basic Microbiol.*, 30(1):37–41, 1990). While this approach can produce large quantities of plasmids, production yield is only proportional to cell mass.

A need exists, to develop economically viable methods for producing plasmids on a large scale to meet the increasing demand.

SUMMARY OF THE INVENTION

This invention relates to an aqueous medium formulation which is capable of allowing the growth of a plasmid-producing host cell to an optical density greater than 30 at 600 nm and, in addition, enhancing plasmid production beyond that which would be expected at the cell densities achieved. The medium of the present invention comprises a carbon source in the concentration range of about 20 to about 40 grams per liter of the water component of the medium.

In another aspect, the present invention relates to a method of increasing a plasmid-producing prokaryotic cell to a density greater than an O.D. reading of 30 at 600 nm and of enhancing the plasmid production of a prokaryotic host cell by culturing the prokaryotic host cell in an aqueous medium with the composition comprising a carbon source in the range as stated above.

BRIEF DESCRIPTION OF THE DRAWING

The FIGURE is a graph of the actual plasmid yield obtained from a culture of prokaryotic cells using the medium of the present invention versus the plasmid yield that would be expected given the cell density.

DETAILED DESCRIPTION OF THE INVENTION

This invention is based upon the discovery that using an aqueous medium formulation with a high concentration of a carbon source increases prokaryotic cell density and plasmid production beyond that achieved using the prokaryotic medium formulations disclosed previously.

The medium of the present invention comprises a carbon source in the concentration range of about 10 to about 40 grams. Suitable carbon sources include glucose, mannose, galactose, maltose and glycerol. Glucose in a concentration of about 30 grams per liter of the water component of the medium is preferred.

It is believed that the medium of the present invention is suitable for any prokaryotic cell. Suitable cells include those belonging to the genuses Norcardia, Bacillus, Corynebacterium and Escherichia.

It should be noted that prokaryotic media formulations in addition to requiring a carbon source need to provide a nitrogen source, a trace metal mixture, a complex vitamin source (although some prokaryotes can produce their own) and an inorganic salt mixture in order to sustain prokaryotic cells in culture.

Suitable nitrogen sources for use in the medium of the present invention include ammonium chloride, primatone CLT, casein enzymatic hydrolysate or any other protein digest. In a preferred embodiment the medium contains about 10.0 g of ammonium chloride, 10.0 g primatone CLT, 20.0 g casein enzymatic hydrolysate each per liter of the water component of the medium.

A suitable trace metal mixture for use in the medium of the present invention would include a mixture of sodium molybdate, manganese sulfate, cupric chloride, cobalt chloride, boric acid and zinc chloride. In a preferred embodiment the mixtures contains 4.0 mg sodium molybdate, 20.0 mg manganese sulfate, 2.0 mg cupric chloride, 8 mg cobalt chloride, 1.0 mg boric acid and 4 mg zinc chloride.

A suitable inorganic salt mixture would include magnesium sulfate, potassium sulfate and ferrous sulfate. In a preferred embodiment the mixtures contains 0.4 g magnesium sulfate, 0.2 g potassium sulfate and 12.7 mg ferrous sulfate A suitable complex vitamin source for use in the medium of the present invention would include a yeast extract such as Bacto yeast extract.

Any method for growing prokaryotic cells known to those skilled in the art is suitable for using the medium formulation of the present invention in the method of present invention. See Gerhardt, P, et al., *Manual of Methods for General Bacteriology*, Published by American Society for Microbiology, 1981.

Any method for determining optical density known to those skilled in the art are suitable in the method of the present invention (see Gerhardt, P,)

EXEMPLIFICATION

Materials and Methods:

Frozen *E. coli* cells containing the appropriate plasmid were used to inoculate 100 ml of Luria-Bertani Medium (LB) (components of which are listed in Table 1 below) in 2×500 ml shake flasks. The culture was incubated at 37+0.5° C. for 15–18 hours on an orbital shaker (New Brunswick Scientific, New Brunswick, N.J.) at 150–250 rpm.

TABLE 1

LB FORMULATION

| # | Components | grams/liter of H₂O |
|---|---|---|
| 1. | Bacto Yeast Extract | 5 |
| 2. | Bacto tryptone | 10 |
| 3. | sodium chloride | 10 |

The seed culture was used to inoculate a 20 liter fermentor containing 15 liters of a medium components of which are listed in Table 2 below:

TABLE 2

THE MEDIA FORMULATION OF THE PRESENT INVENTION

| # | Components | Amount/liter of H₂O |
|---|---|---|
| 1. | glucose | 30.0 g |
| 2. | Bacto Yeast Extract | 20.0 g |
| 3. | ammonium chloride | 10.0 g |
| 4. | potassium phosphate, monobasic | 1.5 g |
| 5. | magnesium sulfate.7H₂O | 0.4 g |
| 6. | potassium sulfate | 0.2 g |
| 7. | Primatone CLT | 10.0 g |
| 8. | Casein Enzymatic Hydrolysate | 20.0 g |
| 9. | Ferrous Sulfate.7H₂O | 12.7 mg |
| 10. | calcium chloride.2H₂O | 4.0 mg |
| 11. | sodium molybdate.2H₂O | 4.0 mg |
| 12. | manganese sulfate | 20 mg |
| 13. | cupric chloride.2H₂O | 2.0 mg |
| 14. | cobalt chloride.6H₂O | 8.0 mg |
| 15. | boric acid | 1.0 mg |
| 16. | zinc chloride | 4.0 mg |
| 17. | Pluoronic 25-R-2 (BASF) | 0.67 ml |
| 18. | ampicillin | 0.1 g |

The culture was allowed to grow for 15 hours under the conditions listed in Table 3 below:

TABLE 3

GROWTH CONDITIONS

| # | Condition | Measure |
|---|---|---|
| 1. | agitation | 800 rpm |
| 2. | aeration | 1.0 + 0.1 vvm |
| 3. | temperature | 37° C. |
| 4. | pH | controlled at 7.0 + 0.1 |

Culture growth was determined by monitoring optical density with a cell density probe (Cerex Co., Jamesville, N. Dak.) at 600 nm until all glucose had been depleted and the optical density had reached 35–40. We allowed the culture to continue until plasmid concentration stopped increasing in around 4 to 8 hours after glucose was depleted. The final O.D. 600 nm reading was 60±5. Harvest of the culture was by centrifugation. The cells were stored at −70° to −80° C. until purification.

Cell Growth and Dried Cell Weight Measurement

Cell growth was determined by monitoring optical density with a cell density probe (Cerex) at 600 nm. Dried cell weight was determined by centrifuging (5000×g for 10 min. at 4° C. 50 ml. culture, washing the cell pellet three times with deionized water and dried in a 60° C. (6–7 hours) hot air over until a constant weight is obtained. The dry cell weight in expressed as gram per liter of culture.

Glucose Measurement

Glucose concentration was measured with a biolyzer (Kodak, Rochester, N.Y.) using the procedure provided by Kodak.

Plasmid Purification

The cells were suspended in Tris/EDTA/RNase A, pH 8 and lysed with NaOH+SDS. Cell debris, proteins and chromosomal DNA were precipitated with 2.5–3M potassium acetate. The plasmid was then purified, using Nucleobond (The Nest Group, Inc., Southboro, Mass.) plasmid purification column following the instructions provided.

Plasmid Analysis

The concentration of plasmid was estimated by measuring absorption at 260 nm. The purity of the plasmid is determined by: 1) ratio of A260/A280, in an acceptable range of 1.8–2.0, Spectophometer (Hewlett Packard, Germany) 2) visual inspection of an ethidium bromide stained agarose gel after electrophoresis, the absence of RNA and genomic DNA bands on the gel indicates good quality. The quality of the plasmid is determined by restriction maps, in vitro transformation of mammalian cells and assaying for the gene product (Maniatis et al.).

Equivalents

Those skilled in the art will recognize, or be able to ascertain, using no more than routine experimentation many equivalents to the specific embodiments of the invention described herein. Such equivalents are intended to be encompassed by the following claims:

We claim:

1. An aqueous medium formulation for the plasmid production of a *Escherichia coli* host cell, the medium comprising about:

a) 30.0 grams of glucose;
b) 20.0 grams of yeast extract;
c) 10.0 grams ammonium chloride;
d) 1.5 grams of potassium phosphate;
e) 0.4 grams of magnesium sulfate;
f) 0.2 grams of potassium sulfate;
g) 10.0 grams of a meat digest;
h) 20.0 grams casein enzymatic hydrolysate;
i) 12.7 milligrams of ferrous sulfate;
j) 4.0 milligrams of calcium chloride;
k) 4.0 milligrams of sodium molybdate;
l) 20.0 milligrams of manganese sulfate;
m) 2.0 milligrams of cupric chloride;
n) 8.0 milligrams of cobalt chloride;
o) 1.0 milligrams of boric acid; and
p) 4.0 milligrams of zinc chloride, per liter of the water component of the medium.

2. In a process for producing plasmids from a *Escherichia coli* host cell wherein the improvement comprises culturing the prokaryotic host cell in an aqueous medium formulation containing about:

a) 30.0 grams of glucose;
b) 20.0 grams of yeast extract;
c) 10.0 grams ammonium chloride;
d) 1.5 grams of potassium phosphate;
e) 0.4 grams of magnesium sulfate;
f) 0.2 grams of potassium sulfate;
g) 10.0 grams of a meat digest;
h) 20.0 grams casein enzymatic hydrolysate;

i) 12.7 milligrams of ferrous sulfate;
j) 4.0 milligrams of calcium chloride;
k) 4.0 milligrams of sodium molybdate;
l) 20.0 milligrams of manganese sulfate;
m) 2.0 milligrams of cupric chloride;
n) 8.0 milligrams of cobalt chloride;
o) 1.0 milligrams of boric acid; and
p) 4.0 milligrams of zinc chloride, per liter of the water component of the medium at about 37° C., a pH of about 7.0 and in a fed-batch culturing mode.

3. A method for the production of plasmids from a *Escherichia coli* host cell, comprising:
  a) culturing the host cell in an aqueous medium containing about:
    i) 30.0 grams of glucose;
    ii) 20.0 grams of yeast extract;
    iii) 10.0 grams ammonium chloride;
    iv) 1.5 grams of potassium phosphate;
    v) 0.4 grams of magnesium sulfate;
    vi) 0.2 grams of potassium sulfate;
    vii) 10.0 grams of a meat digest;
    viii) 20.0 grams casein enzymatic hydrolysate;
    ix) 12.7 milligrams of ferrous sulfate;
    x) 4.0 milligrams of calcium chloride;
    xi) 4.0 milligrams of sodium molybdate;
    xii) 20.0 milligrams of manganese sulfate;
    xiii) 2.0 milligrams of cupric chloride;
    xiv) 8.0 milligrams of cobalt chloride;
    xv) 1.0 milligrams of boric acid; and
    xvi) 4.0 milligrams of zinc chloride;

per liter of the water component of the medium at about 37° C., a pH of about 7.0 and in a fed-batch culturing mode;
  b) allowing production of the plasmids in the host cell;
  c) collecting the medium containing the host cell in step b;
  d) isolating the host cell from the medium;
  e) lysing the host cell to release the plasmids; and
  f) purifying the plasmids released from the host cell in step e.

\* \* \* \* \*